(12) United States Patent
Knifton et al.

(10) Patent No.: US 6,903,044 B2
(45) Date of Patent: Jun. 7, 2005

(54) ONE-STEP PRODUCTION OF 1,3-PROPANEDIOL FROM ETHYLENE OXIDE AND SYNGAS WITH A CATALYST WITH A N-HETEROCYCLIC LIGAND

(75) Inventors: John Frederick Knifton, Houston, TX (US); Talmadge Gail James, Houston, TX (US); Kevin Dale Allen, Prairieville, LA (US); Paul Richard Weider, Houston, TX (US); Joseph Broun Powell, Houston, TX (US); Lynn Henry Slaugh, Houston, TX (US); Timothy Williams, Houston, TX (US)

(73) Assignee: Shell Oil Company, Houston, TX (US)

( * ) Notice: Subject to any disclaimer, the term of this patent is extended or adjusted under 35 U.S.C. 154(b) by 359 days.

(21) Appl. No.: 10/298,866

(22) Filed: Nov. 18, 2002

(65) Prior Publication Data

US 2003/0204118 A1 Oct. 30, 2003

Related U.S. Application Data

(62) Division of application No. 10/146,590, filed on May 15, 2002, now Pat. No. 6,586,643.
(60) Provisional application No. 60/291,826, filed on May 18, 2001.

(51) Int. Cl.$^7$ ............................................. B01J 31/00
(52) U.S. Cl. .................. 502/167; 502/150; 502/152; 502/153; 502/155; 502/161; 502/162; 502/200; 502/326
(58) Field of Search ................ 502/167, 155, 502/150, 152, 153, 161, 162, 200, 326

(56) References Cited

U.S. PATENT DOCUMENTS

| | | | |
|---|---|---|---|
| 3,456,017 A | 7/1969 | Smith et al. ............... | 260/602 |
| 3,463,819 A | 8/1969 | Smith et al. ............... | 260/602 |
| 3,687,981 A | 8/1972 | Lawrence et al. ........ | 260/340.7 |
| 4,238,357 A | 12/1980 | Pesa et al. | |
| 4,433,177 A | 2/1984 | Lin et al. | |
| 4,665,222 A | 5/1987 | Whyman | |
| 4,935,547 A | 6/1990 | Leung et al. | |
| 5,256,827 A | 10/1993 | Slaugh et al. ............. | 568/454 |
| 5,304,686 A | 4/1994 | Slaugh et al. ............. | 568/496 |
| 5,304,691 A | 4/1994 | Arhancet et al. ......... | 568/867 |
| 5,344,993 A | 9/1994 | Slaugh et al. ............. | 568/454 |
| 5,459,299 A | 10/1995 | Cheng ....................... | 219/267 |
| 5,463,144 A | 10/1995 | Powell et al. ............. | 568/867 |
| 5,463,145 A | 10/1995 | Powell et al. ............. | 568/867 |
| 5,463,146 A | 10/1995 | Slaugh et al. ............. | 568/852 |
| 5,545,765 A | 8/1996 | Slaugh et al. ............. | 568/862 |
| 5,545,766 A | 8/1996 | Powell et al. ............. | 568/862 |
| 5,545,767 A | 8/1996 | Weider et al. ............. | 568/867 |
| 5,563,302 A | 10/1996 | Weider et al. ............. | 568/862 |
| 5,585,528 A | 12/1996 | Powell et al. | |
| 5,689,016 A | 11/1997 | Weider et al. ............. | 568/862 |
| 5,841,003 A | 11/1998 | Slaugh et al. | |

FOREIGN PATENT DOCUMENTS

| | | |
|---|---|---|
| WO | WO 94/18149 | 8/1994 |
| WO | WO 96/10552 | 4/1996 |

OTHER PUBLICATIONS

Chemical Abstracts Service, Columbus, Ohio, US, Matsuzaka, H. et al., "Chemistry of Cobalt–Ruthenium Mixed Metal Clusters and Mixed Metal Complexes," retrieved from STN Database Accession No. 1988:535737 XP002220900, Abstract, Structure, Nippon Kagaku Kaishi, No. 5, May 1988, pp. 705–713, XP002220899, ISSN: 0369–4577 Abstract; Figures 2, 7–9; Table 3.
International Search Report of Dec. 2, 2002.
U.S. Appl. No. 09/808,974, filed Mar. 15, 2001, Knifton et al.
U.S. Appl. No. 10/158,452, filed May 30, 2002, Knifton et al.
U.S. Appl. No. 10/146,675, filed May 15, 2002, Knifton et al.
U.S. Appl. No. 09/963,068, filed Sep. 25, 2001, Allen et al.

*Primary Examiner*—Johann R. Richter
*Assistant Examiner*—Elvis O. Price
(74) *Attorney, Agent, or Firm*—Donald F. Haas

(57) ABSTRACT

Disclosed is a new catalyst composition comprising a bimetallic Co—Ru catalyst complexed with a N-heterocylcic ligand that is effective, economical, and provides improvements in oxidative stability in the one step synthesis of 1,3-propanediol (1,3-PDO) from ethylene oxide and synthesis gas. For example, cobalt-ruthenium-2,2'-bipyrimidine, 2,2'-dipyridyl, or 2,4,6-tripridyl-s-triazine catalyst precursors in cyclic ether solvents, such as 1,3-dioxolane, 1,4-dioxolane, 1,4-dioxane, and 2-ethyl-2-methyl-1,3-dioxolane, provide good yields of 1,3-PDO in a one step synthesis.

32 Claims, 5 Drawing Sheets

ONE-STEP PRODUCTION OF 1,3-PROPANEDIOL FROM ETHYLENE OXIDE AND SYNGAS WITH A CATALYST WITH A N-HETEROCYCLIC LIGAND

This is a division of application Ser. No. 10/146,590 filed May 15, 2002 now U.S. Pat. No. 6,586,643 which claims benefit of U.S. Provisional Application No. 60/291,826 filed May 18, 2001, the entire disclosure of which is hereby incorporated by reference.

FIELD OF INVENTION

This invention relates to the synthesis of an aliphatic 1,3-diol, particularly 1,3-propanediol, from ethylene oxide and syngas in one step. More particularly this invention relates to a catalyst that provides good yields under mild conditions in the one-step synthesis of 1,3-propanediol and demonstrates advantages with respect to cost and oxidative stability. The catalyst of the invention comprises a homogeneous bimetallic cobalt-ruthenium catalyst, plus a N-heterocyclic ligand, or multidentate N-heterocyclic ligand.

BACKGROUND OF THE INVENTION

Aliphatic 1,3-diols, particularly 1,3-propanediol, have many applications as monomer units for polyester and polyurethane, and as starting materials for the synthesis of cyclic compounds. For example, CORTERRA® polymer is a polyester characterized by outstanding properties that is made of 1,3-propanediol (hereafter 1,3-PDO) and terephthalic acid. There is much interest in the art in finding new routes for synthesizing 1,3-PDO that are efficient, economical, and demonstrate process advantages.

U.S. Pat. Nos. 3,463,819 and 3,456,017 teach the hydroformylation of ethylene oxide to produce 1,3-propanediol and 3-hydroxypropanal (hereafter 3-HPA) using a tertiary phosphine-modified cobalt carbonyl catalyst.

U.S. Pat. No. 5,304,691, assigned to Shell, discloses a method of hydroformylating ethylene oxide to 3-hydroxypropanal and 1,3-propanediol in a single step using an improved catalyst system comprising a cobalt-tertiary phosphine ligand in combination with a ruthenium catalyst. In '691 1,3-PDO and 3-HPA are produced by intimately contacting an oxirane, particularly ethylene oxide (hereafter EO), a ditertiary phosphine-modified cobalt carbonyl catalyst, a ruthenium catalyst promoter, and syngas (carbon monoxide and hydrogen) in an inert reaction solvent at hydroformylation reaction conditions. A PDO yield of up to 86–87 mole % is reported, using a catalyst comprising cobalt ligated with 1,2-bis (9-phosphabicyclononyl) ethane as bidentate ligand, and either triruthenium(0) dodecacarbonyl or bis[ruthenium tricarbonyl dichloride] as cocatalyst.

The production of 1,3-PDO in one step with minimal impurities and byproducts involves recycle and requires a catalyst system with good stability both during 1,3-PDO synthesis and during product recovery and recycle. It would be very desirable if a catalyst system were available that produced 1,3-PDO in one step, in good yields, and was characterized by greater oxidative stability during 1,3-PDO synthesis and recycle. In addition, phosphine ligands are relatively expensive and it would be desirable to have the option of a ligand system that provided the aforementioned advantages, but was less expensive.

SUMMARY

In accordance with the foregoing, the present invention provides an alternative to the use of phosphine ligands in a hydroformylation catalyst composition. The ligands of the present invention provide a less expensive alternative, have the ability to form stable complexes with Group VIII transition metals, and provide good oxidative stability. The invention is a catalyst composition comprising:

a) A cobalt component comprising of one or more non-ligated cobalt carbonyl compounds; and b) A ruthenium component comprising a ligated ruthenium carbonyl compound wherein said ligand is selected from a N-heterocyclic or multidentate N-heterocyclic moiety.

Bidentate and multidentate N-heterocyclics offer the potential advantages of greater oxidative stability, commercial availability (at least in certain cases), potentially lower cost, and the ability to form stable complexes with Group VIII transition metals. For example, 2,2'-dipyridyl-ruthenium complexes, among others, have been demonstrated to exhibit long-term stability under hydroformylation (synthesis gas pressure conditions).

The novel oxirane hydroformylation catalyst of the present invention involves a complex which is postulated to be a ruthenium-N-heterocyclic ligand: cobalt complex. The characterizing feature of the new catalyst is the use of a bidentate or multidentate N-heterocyclic ligand ligated to ruthenium rather than cobalt, as is the case in U.S. Pat. No. 5,304,691.

The invention also provides a one step process for preparing a 1,3-diol, comprising the reaction of an oxirane with syngas at hydroformylation conditions in an inert solvent in the presence of the catalyst complex of this invention.

DETAILED DESCRIPTION OF THE INVENTION

Figure 1:
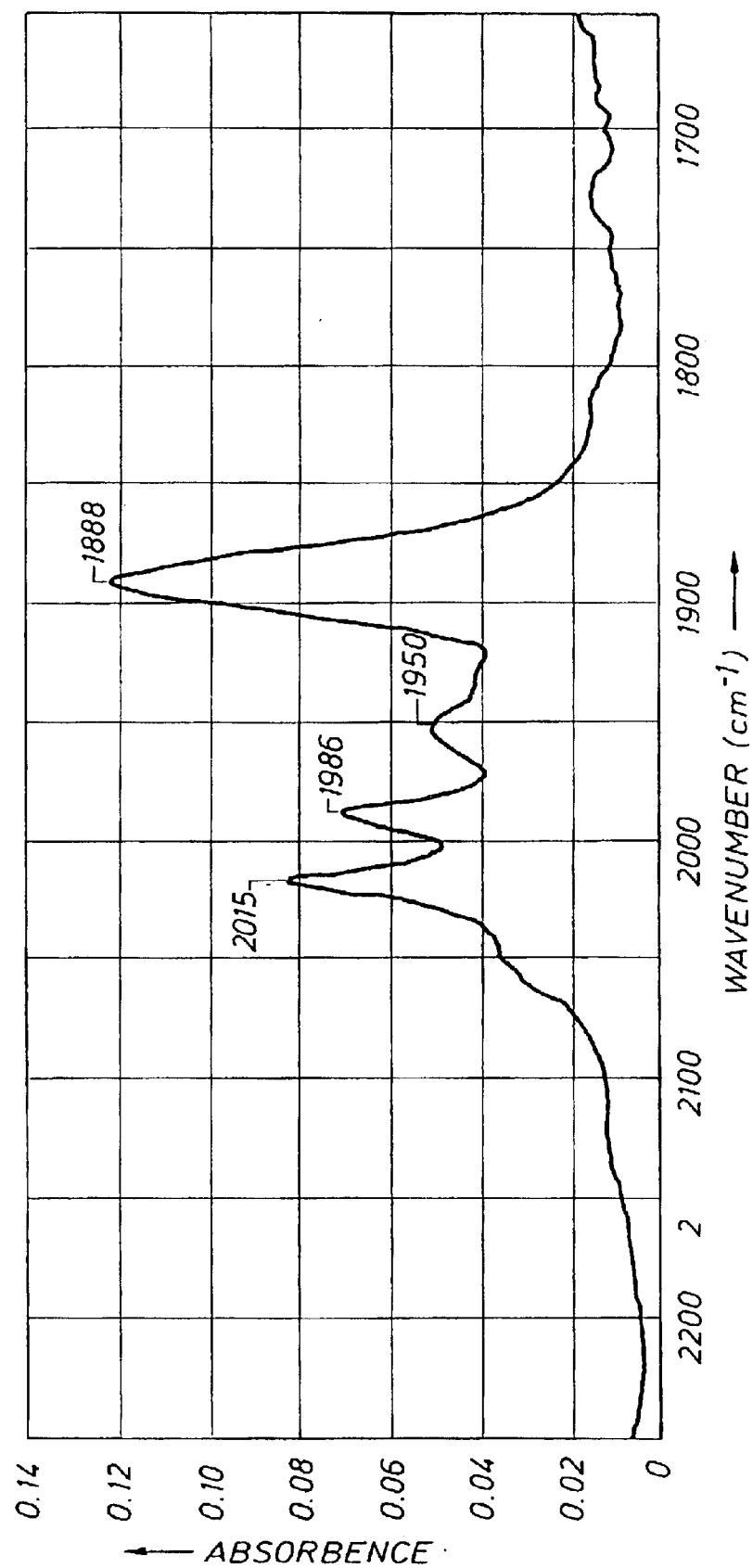
FIG. 1 is an IR spectrum of the cobalt-ruthenium-2,4,6-tripyridyl-s-triazine (TPTZ) catalyst after preforming in 1,3-dioxolane.
Figure 2:
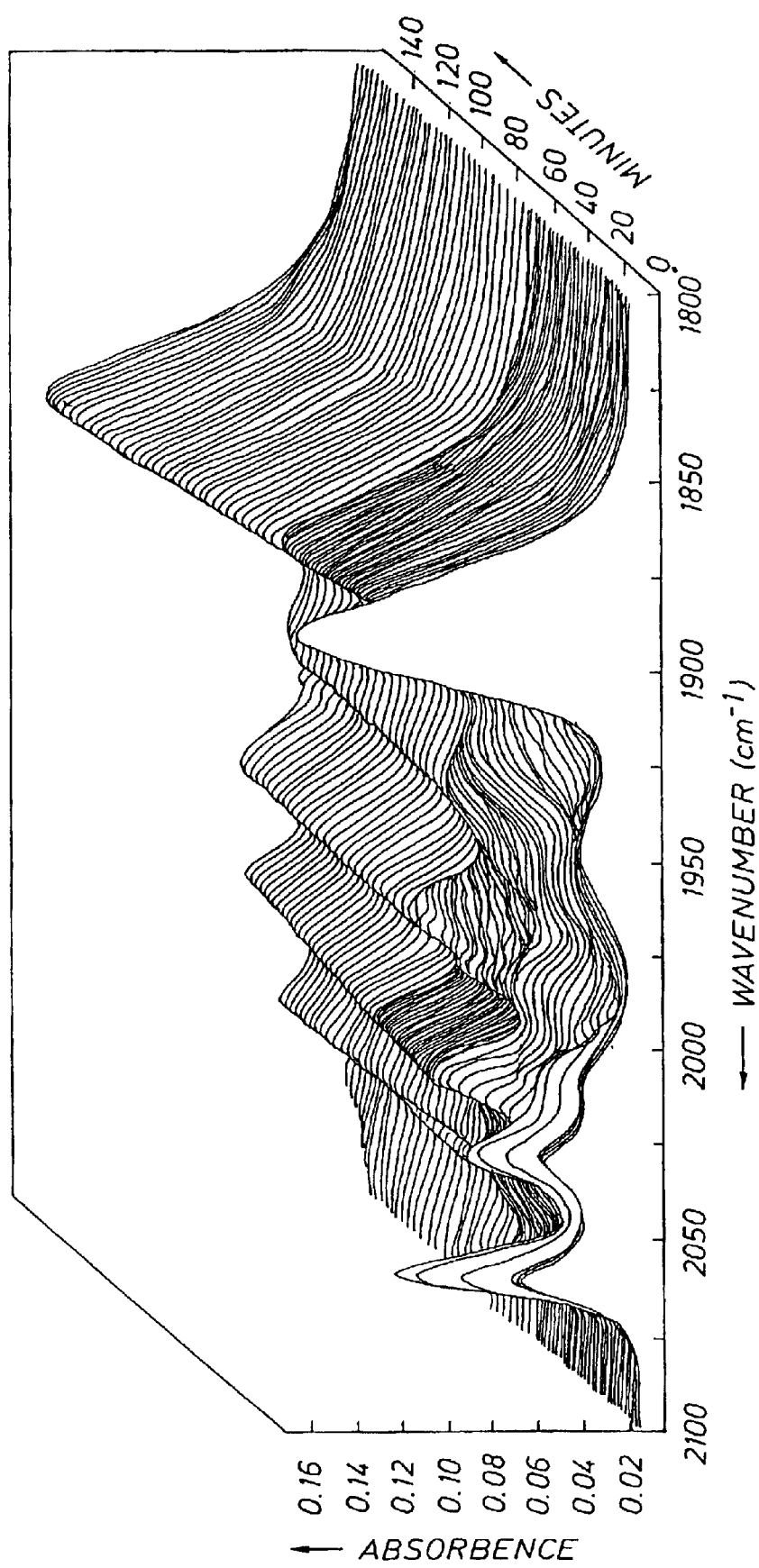
FIG. 2 is an IR cascade plot showing the formation of the Co—Ru-TPTZ catalyst as a function of time.
Figure 3:
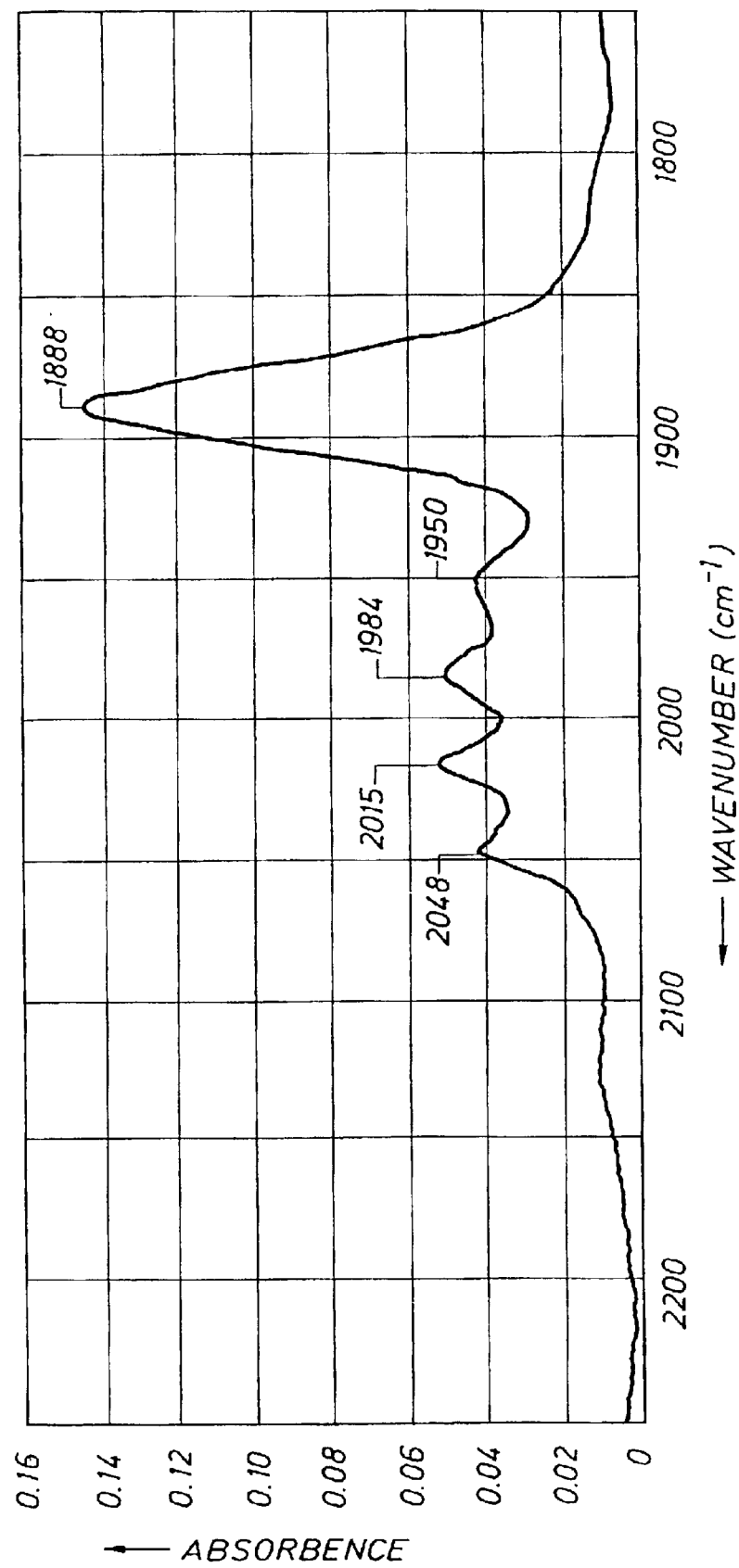
FIG. 3 shows the IR spectrum of the Co—Ru-TPTZ catalyst during the one-step conversion of ethylene oxide and synthesis gas to 1,3-propanediol.
Figure 4:
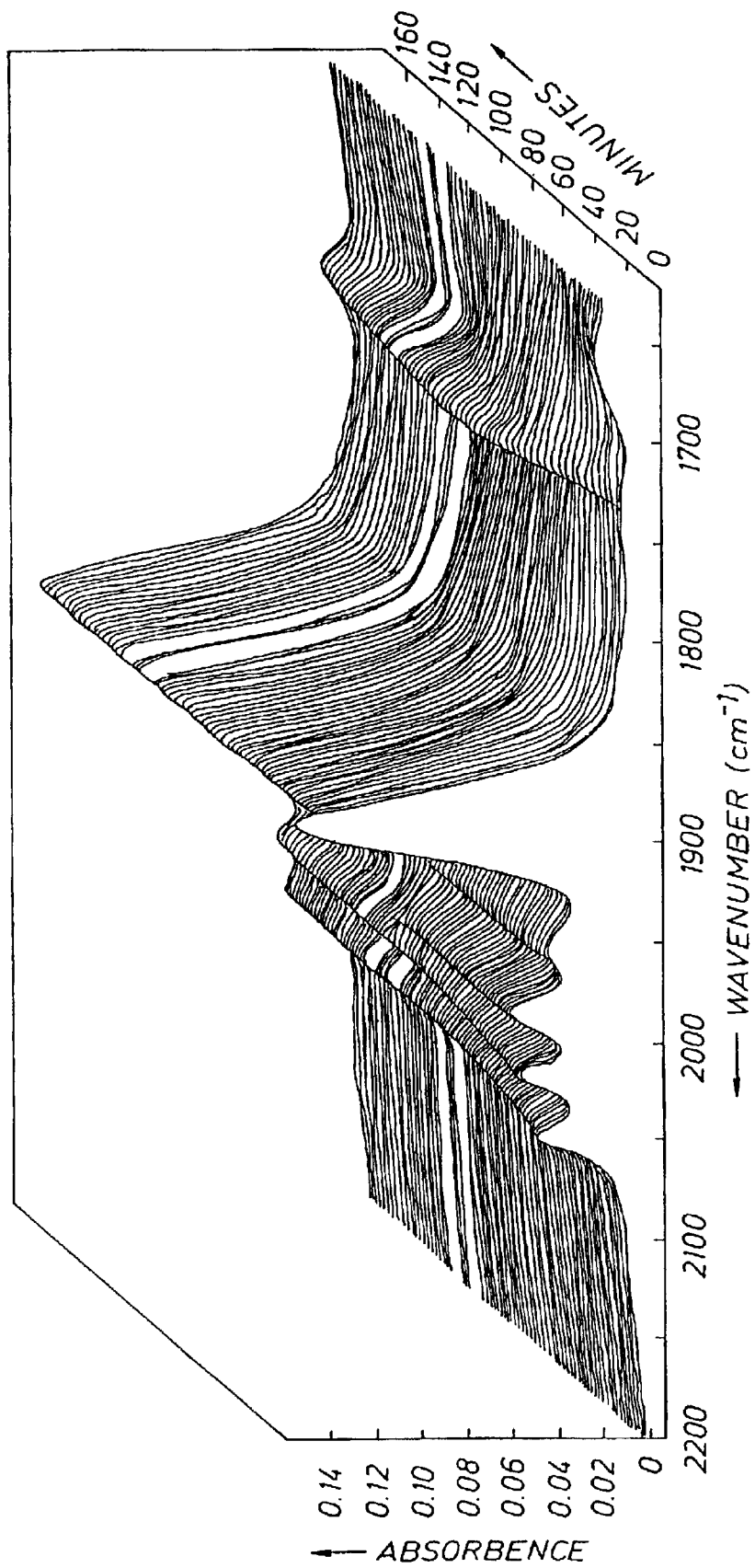
FIG. 4 is an IR cascade plot showing the Co—Ru-TPTZ catalyst during the one-step 1,3-PDO synthesis.

The selective hydroformylation/hydrogenation of ethylene oxide to 1,3-PDO in one step, represented by:

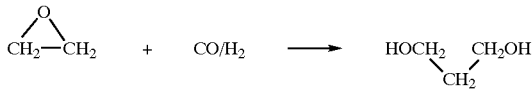

has been demonstrated using a cobalt-ruthenium homogeneous catalyst system in conjunction with soluble bidentate or multidentate N-heterocyclic ligands. N-heterocyclic ligands that provide good results, include, for example, the commercially available 2,2'-dipyridyl, 2,2'-bipyrimidine, and 2,4,6-tripyridyl-s-triazine.

The one-step process for synthesizing 1,3-PDO generally comprises intimately contacting ethylene oxide, carbon monoxide and hydrogen (syngas), and a bimetallic catalyst in a liquid-phase solution in an inert reaction solvent at a temperature of from about 30 to 150° C., and an elevated pressure.

The use of the new Co—Ru—N-heterocyclic system requires certain synthesis changes in comparison with work where a phosphine ligand is ligated to a Co compound, such as U.S. Pat. No. 5,304,691. Important aspects of the one-step process of the present invention include the need for particular solvents, the use of hydrogen-rich synthesis gas, and operation at a somewhat higher pressure. Preferred solvents include cyclic aliphatic ethers. Preferred operating pressure is closer to 2000 psi (13,790 kPa), whereas in the case of the phosphine ligated Co the preferred pressure is closer to 1500 psi (10,340 kPa).

Other important factors in the development of this chemistry include efficient PDO recovery from the crude oxonated product solutions, and recycle of the active Co—Ru—N-heterocyclic catalyst.

The 1,3-diols are made by charging an oxirane, catalyst, optional cocatalyst and/or catalyst promoter, and reaction solvent to a pressure reactor with the introduction of syngas (a mixture of hydrogen and carbon monoxide, suitably in a molar ratio of 1:1 to 8:1, preferably 2:1 to 6:1) under hydroformylation conditions.

The process of the present invention may be carried out as a batch-type process, continuous process, or a combination thereof.

In the preferred embodiment of the present invention separate, combined, or staged streams of EO, syngas, and catalyst are charged to a reaction vessel, which can be a pressure reaction vessel such as a bubble column or a stirred autoclave, operated batch-wise or in a continuous manner.

Oxiranes of up to 10 carbon atoms, preferably up to 6 carbon atoms, and ethylene oxide in particular may be converted into their corresponding 1,3-diols by the hydroformylation reaction with syngas in the presence of the catalyst complex of the present invention.

An essential part of the present invention is the use of the Co—Ru-bidentate or multidentate N-heterocyclic complex. The complex of the present invention is believed to comprise a novel class of ruthenium-modified catalysts. The characterizing feature of this novel class involves an oxidized ruthenium metal that is ligated to a bidentate or multidentate N-heterocyclic ligand, with a cobalt compound as the counter ion.

The oxidation state of the ruthenium atom is not entirely certain (in theory, ruthenium may have a valence of 0 to 8), which may even change during the course of the hydroformylation reaction. Accordingly, the molar ratio of ruthenium to cobalt may vary within relatively broad ranges. Sufficient cobalt(0) should be added to completely oxidize all of the complexed ruthenium employed. An excess of cobalt can be added, but is not of particular value. Suitably, the molar ratio varies from 4:1 to 1:4, preferably from 2:1 to 1:3, more preferably from 1:1 to 1:2.

A large number of N-heterocyclic compounds have been identified as suitable ligands for the one step PDO synthesis using the cobalt-ruthenium catalyst couple. Suitable types of bidentate and multidentate N-heterocyclic ligands include, but are not limited to:

Diazines such as pyrimidine, pyrazine, pyridazine, as well as benzodiazines such as quinazoline and quinoxaline; bispyridines such as 2,2'-dipyridyl (DIPY), 2,2'-bipyrimidine (BPYM), 1,10-phenanthroline (PHEN), di-2-pyridyl ketone, 4,4'-dimethyl-2,2'-dipyridyl, 5,6-dimethylphenanthroline, 4,7-dimethylphenanthroline, 2,2'-biquinoline, neocuproine, and 2,2'-dipyridylamine; multipyridines such as 2,4,6-tripyridyl-s-triazine (TPTZ), 3,6-di-2-pyridyl-1,2,4,5-tetrazine, 2,2':6',2"-terpyridine, 2,3-bis(pyridyl)pyrazine, and 3-(2-pyridyl)-5,6-diphenyl-1,2,4-triazine; pyridine, 3-hydroxypyridine, and quinoline, particularly the lower cost homologues derived from coal-tar extracts; and certain 2,6-pyridyl-diimines such as 2,6-bis(N-phenyl, methylimino)pyridine and 2,6-bis[N-(2,6-diisopropylphenyl)methylimino]pyridine.

Good results were demonstrated in the examples herein using 2,2'-dipyridyl (DIPY), 2,2'-bipyrimidine (BPYM), and 2,4,6-tripyridyl-s-triazine (TPTZ). The structures of these three N-heterocyclics are as follows:

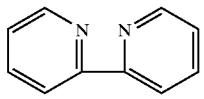 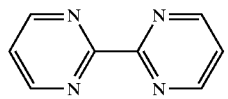

DIPY    BPYM

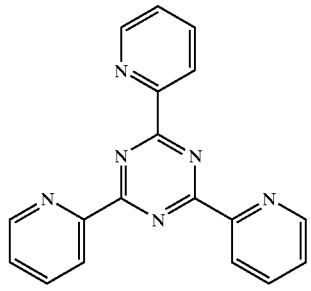

TPTZ

Suitable cobalt sources also include salts that are reduced to the zero valence state by heat-treatment in an atmosphere of hydrogen and carbon monoxide. Examples of such salts comprise, for instance, cobalt carboxylates such as acetates, octanoates, etc., which are preferred, as well as cobalt salts of mineral acids such as chlorides, fluorides, sulfates, sulfonates, etc. Operable also are mixtures of these cobalt salts. It is preferred, however, that when mixtures are used, at least one component of the mixture be a cobalt alkanoate of 6 to 12 carbon atoms. The reduction may be performed prior to the use of the catalysts, or it may be accomplished simultaneously with the hydroformylation process in the hydroformylation zone.

The counter ion, for best results, is believed to be the cobalt tetracarbonyl anion, ([Co(CO)$_4$]$^-$), having a characteristic cobalt carbonyl IR band in the region 1875 to 1900 cm$^{-1}$, particularly in the region 1888 cm$^{-1}$. However, this ion in the active catalyst can be a modification thereof. Part of the cobalt compound may be modified with N-heterocyclic ligand, e.g., up to 75 mole % excess, say up to 50 mole % or less. However, the counter ion is preferably the non-ligated cobalt tetracarbonyl anion mentioned before. Cobalt carbonyls can be generated by reaction of a starting cobalt source such as cobalt hydroxide with syngas, as described in J. Falbe, "Carbon Monoxide in Organic Synthesis", Springer-Verlag, NY (1970), which is herein incorporated by reference or otherwise.

The molar stoichiometry ratio of cobalt:ruthenium:N-ligand is suitably in the range of 0.5 to 4 moles cobalt: 0.3 to 2 moles ruthenium: 0.1 to 2 moles N-ligand. A preferred range would be about 1 to 3 moles cobalt to 0.5 to 1.5 moles ruthenium to 0.5 to 1 moles N-ligand. A formulation that worked well, for example, was cobalt: ruthenium: 2,4,6-tripyridyl-s-triazine in molar stoichiometry of 2:1:0.7, respectively. A preferred formulation is cobalt: ruthenium: 2,2'-bipyrimidine or 2,2'-dipyridyl in a molar stoichiometry of 2:1:1 to 1:1:1. Unligated ruthenium carbonyl is believed to be a far less active species, and the catalyst preparation therefore seeks to ligate each ruthenium atom.

The catalyst complex, can be made as follows: The first step in the catalyst preparation is synthesis of the Ru—N-ligand complex. This may be done by bringing a suitable Ru(0) source, e.g., triruthenium dodecacarbonyl, in contact with the N-heterocyclic ligand. Alternatively, the triruthenium dodecacarbonyl may be replaced with other readily available ruthenium carbonyl derivatives, such as ruthenium dicarbonyl acetate polymer and ruthenium(II) tricarbonyl dichloride, dimer. Further alternatives include the use of less expensive ruthenium sources that, under a syngas atmosphere, will in-situ form ruthenium carbonyl species. These less expensive ruthenium sources may include ruthenium(IV) oxide, hydrate, ruthenium(III) chloride, and ruthenium-on-carbon.

The conditions at which these compounds are allowed to form a complex are not critical. Temperature and pressure may vary within the ranges given below with respect to the hydroformylation reaction, for example 25 to 150° C. Syngas may be used as gas cap during the complex formation. It is preferable to use a solvent, preferably the solvent used in the hydroformylation reaction. Obviously, this solvent should be capable of dissolving the active catalyst, without affecting its properties. Suitable solvents include the ethers described below for use in the hydroformylation process, in particular cyclic aliphatic ethers.

The ruthenium-N-heterocyclic ligand may for instance be made by reacting triruthenium dodecacarbonyl with a stoichiometric amount of a selected N-heterocyclic ligand in a solvent at a temperature within the range of 25 to 150° C., suitably 100 to 110° C. under a carbon monoxide or synthesis gas atmosphere, for 1 to 24 hours (i.e. until completion). At this point, optionally, said ruthenium-N-heterocyclic complex may be isolated as a discrete material.

Next, the Ru—N-heterocyclic ligand complex is brought into contact with a suitable cobalt carbonyl compound by means of a redox reaction to form the Ru—Co—N-ligand complex, again at the aforementioned (noncritical) conditions. A suitable cobalt source is dicobalt octacarbonyl, but other cobalt complexes and salts may be used as well. For instance, the selected cobalt carbonyl, and optional promoters, if any, are added to the solution which is then maintained at the elevated temperature (from 25 to 150° C.) for a time of about 15 minutes to 24 hours. This process is referred to as a step-wise preparation method. Again, optionally, the new cobalt-ruthenium-N-heterocyclic complex may be isolated and characterized.

It is also within the scope of the present invention to prepare the cobalt-ruthenium-N-heterocyclic complex by a self-assembly method, wherein all catalyst components are brought together at the same time. The cobalt-ruthenium-N-heterocyclic complexes may be generated by self-assembly, in one step, when solubilized in a suitable ether solvent under synthesis gas conditions, but the conditions and, in particular, the solvent, are selected such as to favor the formation of a ligated ruthenium species, rather than a ligated cobalt species. The presence of the Ru-ligated species rather than the Co-ligand species may be confirmed by e.g. IR analysis. Typically, whether said active Co—Ru—N-heterocyclic catalyst is generated step-wise, or by self assembly, it exhibits characteristic IR bands in the metal-carbonyl region, particularly a strong cobalt carbonyl band in the region 1875 to 1900 cm$^{-1}$ due to the $[Co(CO)_4]^-$ anion, plus a series of three or four ruthenium-carbonyl bands in the 1900 to 2100 cm$^{-1}$ region that are postulated to be due to cationic ruthenium carbonyl species. Typical spectra for the Co—Ru-TPTZ catalyst system in 1,3-dioxolane, both during the preparation of said catalyst, and during the EO/syngas reaction to give 1,3-PDO, are illustrated in the accompanying FIGS. 1–4.

The optimum ratio of oxirane in the feed to Ru—Co—N-ligand complex will in part depend upon the particular complex employed. However, molar ratios of oxirane to the cobalt within the Ru—Co—N-ligand complex from 2:1 to 10,000:1 are generally satisfactory, with molar ratios of from 50:1 to 500:1 being preferred.

The reaction solvent should be inert, meaning that it is not consumed during the course of the reaction. Ideal solvents for the invention process will solubilize the feed and products during the course of the reaction, but allow phase separation at reduced temperatures. Suitable solvents are described in U.S. Pat. No. 5,304,691 incorporated herein by reference in the entirety. Good results may be achieved with ethers, particularly cyclic, aliphatic ethers, optionally in combination with an alcohol, such as ethanol or tert-butanol, and/or an aromatic hydrocarbon, such as toluene and the chlorobenzenes.

The summary data in Tables 1 and 2 illustrate the important yield and selectivity advantages of using certain cyclic ether solvents such as, for example, but not limited to, the five-membered ring, 1,3-dioxolane, the six-membered ring, 1,3-dioxane, and 1,4-dioxane (see examples 1 to 16), versus a non-cyclic ether such as methyl tert-butyl ether (MTBE, see example 17). 1,3-Dioxane is of particular interest since it can be readily generated through condensation of 1,3-PDO with formaldehyde. 2-Ethyl-2-methyl-1,3-dioxolane proved to be a particularly interesting solvent choice since it allows PDO product phase separation under normal operating conditions (see example 16). Here the PDO is concentrated in a PDO-rich phase in ca. 36% concentration. The estimated 1,3-PDO yield is 58 mole % and the PDO selectivity 54–73%.

Promoters may be employed. Suitable promoters are described in U.S. Pat. No. 5,304,691, previously cited. Examples of promoters that work well, are readily available, and have demonstrated the promotion of EO conversion are tertiary amines such as N,N-dimethyldodecylamine and triethylamine, as well as alkali salts such as sodium acetate.

For best results, the one step hydroformylation/hydrogenation is conducted under conditions of elevated temperature and pressure. Reaction temperatures range from 30 to 150° C., preferably from 50 to 125° C., and most preferably from 60 to 110° C.

The reaction pressure (total pressure, or partial pressure if inert gaseous diluents are used) should be at least 100 psi (690 kPa). A suitable operating pressure is in the range of 100 psi (690 kPa) to 4000 psi (27,580 kPa), preferably from 1500 psi (10,340 kPa) to 2500 psi (17,240 kPa.), and most preferably about 2000 (13,790 KpA) psi ±250 psi (1725 kPa). In a batch process, the reaction will generally be complete within 1.5 to 5 hours.

The components of the feed streams are contacted in a suitable reaction solvent in the presence of the catalyst complex of the present invention. The EO will preferably be maintained throughout the reaction in a concentration not less than about 0.2% by weight, generally within the range of 0.2 to 20% by weight, preferably 1 to 10% by weight, based on the total weight of the reaction mixture. The process of the invention can be carried out in a continuous mode, while maintaining said EO concentration, by for instance, staged EO addition.

At the conclusion of the hydroformylation reaction, the product mixture is recovered by conventional methods such as selective extraction, fractional distillation, phase separation, selective crystallization, and the like. The unreacted starting materials as well as the catalyst and reaction solvent may, and preferably are, recycled for further use.

Partitioning of the reaction mixture can be promoted by the addition of a phase-split inducing agent. Suitable agents include glycols such as ethylene glycol and linear alkanes such as dodecane. Such an agent will be added to the reaction mixture in an amount within the range of about 2 to 10% by weight, preferably 4 to 8% by weight, based on the total reaction mixture. Alternate methods include addition of 1,3-propanediol into the reaction mixture to bring product concentration up to the target proportion. Also, miscibilizing alcohols and agents with similar polarity such as ethanol, propanol and isopropanol can be added initially, and then removed prior to the subsequent inducing of the phase separation.

Commercial operation will require efficient catalyst recovery with multiple cycles of essentially complete recycle of catalyst to the reaction. The preferred catalyst recovery process involves separation of the two liquid phase mixture noted previously and recycle of the bulk solvent phase to the reactor and return therewith of at least 60 to 90% by weight of the starting catalyst.

In a preferred manner of running the process, reaction conditions such as oxirane concentration, catalyst concentration, solvent, product concentration, reaction temperature and the like are selected so as to achieve a homogeneous reaction mixture at elevated temperatures and cause a partitioning of the reaction mixture into an upper solvent phase containing much of the catalyst and a lower phase containing most of the 1,3-propanediol upon cooling the mixture. Such a partitioning facilitates isolation and recovery of product, recycle of catalyst and removal of heavy ends from the solvent system. This process is referred to as a phase separation catalyst recycle/product recovery method.

In this process, the reactor contents are allowed to settle or are transferred to a suitable vessel at pressures ranging from atmospheric to near reaction pressure where, upon slight or considerable cooling, distinct phases may form that are substantially different, being considerably rich in product, or in catalyst and solvent. The phase rich in catalyst and solvent is directly recycled for further reaction with feed materials. Product is recovered from the product rich phase by conventional methods.

It is preferable that the reaction is run such that product diol maintains concentration levels in the reaction mix suitable for phase separation. For example, concentration of 1,3-propanediol can be between less than 1 and greater than 50% by weight, generally between 8 and 32% by weight, and preferably between 16 and 20% by weight. Temperature during quiescent settling of phases can be between just above the freezing point of the reaction mixture up to at least 150° C., and maybe higher, generally between 27 and 97° C., and preferably between 37 and 47° C. The EO concentration is maintained to avoid the formation of light alcohols and aldehydes that are miscibilizing agents. Oxiranes will preferably be maintained throughout the reaction in a concentration not less than about 0.2% by weight, generally within the range of 0.2 to 20% by weight, preferably 1 to 10% by weight, based on the total weight of the reaction. The reaction can be run with a two-phase system. However, yields and selectivities are maximized when high concentrations of product are present in a single phase reaction and subsequent phase separation occurs upon cooling.

Formulations containing both bidentate and multidentate ligands performed well. Good results have been demonstrated with bimetallic cobalt-ruthenium catalysts in combination with a variety of bidentate N-heterocyclic ligands when solubilized in suitable ether solvents. The cobalt-ruthenium-2,2'-bipyrimidine and 2,2'-dipyridyl catalyst precursors are particularly effective (see, for example, the data in Tables 1 and 2).

Good results have also been realized with multidentate N-heterocyclic ligands, for example, using the cobalt-ruthenium-2,4,6-tripyridyl-s-triazine (TPTZ) catalyst precursor, in cyclic ether solvents such as 1,3-dioxolane, 1,3-dioxane, 1,4-dioxane, and 2-ethyl-2-methyl-1,3-dioxolane (again see data in Table 1).

An in situ infra-red study of the cobalt-ruthenium-2,4,6-tripyridyl-s-triazine catalyst in 1,3-dioxolane (example 58, Table 10), shows the formation of four characteristic bands in the metal-carbonyl region at 1888, 1950, 1986, and 2015 $cm^{-1}$ during preforming of the active species at 90° C. under synthesis gas ($CO/H_2$, 1:4). After addition of ethylene oxide, the reaction mixture at 90° C., again under synthesis gas pressure, continues to exhibit a strong band at 1888 $cm^{-1}$, plus additional bands at 1950, 1984, 2015, and 2048 $cm^{-1}$. This band pattern remains during 1,3-propanediol formation. Typical IR spectra, plus cascade plots, are shown in FIGS. 1–4.

The following examples will serve to illustrate the invention disclosed herein. The examples are intended only as a means of illustration and should not be construed as limiting the scope of the invention in any way. Those skilled in the art will recognize many variations that may be made without departing from the spirit of the disclosed invention.

EXAMPLES 1–20

Examples 1–20 were conducted in a 300 cc capacity Parr reactor system, integrated into a syngas manifold. In examples 1–12 the N-heterocyclic ligand is varied, but only two cyclic ether solvents are employed. In examples 13–20 the solvent is varied. Variations in other components and conditions are noted. Data are given in Tables 1 and 2.

As previously mentioned, particularly good results were demonstrated using 2,2'-dipyridyl (DIPY), 2,2'-bipyrimidine (BPYM), and 2,4,6-tripyridyl-s-triazine (TPTZ). Summary data for the use of these three N-heterocyclics, plus 1,10-phenanthroline (PHEN), in the one-step PDO synthesis are provided in Table 1. Here PDO yields are calculated on a molar basis, based upon the quantity of ethylene oxide charged, while PDO selectivities are estimated by gas chromatograph (GC) analysis of the crude product fractions. The primary co-products include ethanol (the major co-product fraction), HPA intermediate, acetaldehyde, and a small quantity of heavies that include 3-hydroxypropyl-2-hydroxyethyl ether, 3-hydroxypropyl 3-hydroxypropionate, and a PDO/EG ester of 3-hydroxypropionate (all confirmed by GC-ms/IR). The promoter was N,N-dimethyldodecylamine ($Me_2C_{12}N$). In Table 1, example 1, conducted at 90° C. with 1800 psi (12,410 kPa) of ½ ($CO/H_2$) syngas, the 1,3-PDO yield is 49 mole %, basis EO charged, the PDO/HPA product ratio is 26, and the 1,3-PDO/EtOH ratio is 9. Acetaldehyde concentration in the crude product liquid is only 0.3%. In the first Co—Ru-DIPY example (see example 2, Table 1), conducted at 90° C., with 2000 psi (13,790 kPa) of ¼ (CO/H$_2$) syngas, the 1,3-PDO molar yield is 54%, the estimated PDO/ethanol wt ratio is 13, the PDO/HPA ratio is ca. 2.8, and the acetaldehyde concentration in the crude product liquid is 0.8%. Total PDO plus HPA molar yield is ca. 74%, while the dark purple product solution shows no signs of precipitates and the reactor is clean. Multiple ethylene oxide additions, (as in example 5), raise the PDO yield to 66 mole %, and here the PDO/HPA ratio in the final product is >100.

With TPTZ as the added N-heterocycle, hydrogenation of the intermediate HPA is near quantitative and in both examples 7 and 8 the PDO/HPA ratio is >100. 1,3-PDO yields are typically 57–59 mole %. Using 1,4-dioxane as the solvent, as in example 8, the 1,3-PDO/EtOH ratio is 7 and the acetaldehyde make is also below 0.1%. Basis in situ IR studies, we see no evidence for precipitates with this N-heterocycle, either during the Co—Ru-TPTZ catalyst preparation stage, or during the PDO generation phase. Product distributions were again confirmed by GC-ms/IR.

A particular advantage in the use of 2,2'-dipyridyl is that it is commercially available from, for example, Zeneca Corporation or Sigma-Aldrich. A sample of DIPY (97% purity) from Zeneca Corporation (see example 9, Table 1, PDO/HPA ratio 6.6, PDO/EtOH ratio 14) performed similarly to our original samples from Aldrich. Further purification of the Zeneca material through hexane recrystallization (m.p. 69–71° C.) had only a marginal effect upon its performance in PDO service (see example 10, PDO/HPA ratio again 6.6). A second improvement in costs may be realized by using ruthenium dioxide, hydrate as the ruthenium source and generating the ruthenium carbonyl precursors in situ (example 11) by pretreatment at 160° C. with CO-rich gas, PDO+HPA molar yields are then >65%, PDO/EtOH ratio is 15, and acetaldehyde concentration 0.5%. Another alternative is to use ruthenium-on-carbon (example 12, from Alfa), although here the supernatant liquid product typically shows ca. 910 ppm ruthenium.

TABLE 1

| EXP. | CATALYST COMPOSITION | Co:Ru:N | SOLVENT | Me$_2$C$_{12}$N | CONDITIONS | PDO SEL. (%) | PDO YIELD (mole %) |
|---|---|---|---|---|---|---|---|
| 1 | Co$_2$(CO)$_8$—Ru$_3$(CO)$_{12}$—BPYM | 2:1:2 | 1,3-dioxolane | No | a | 61 | 49 |
| 2 | Co$_2$(CO)$_8$—Ru$_3$(CO)$_{12}$—DIPY | 1:1:2 | " | Yes | b | 61 | 54 |
| 3 | Co$_2$(CO)$_8$—Ru$_3$(CO)$_{12}$—DIPY | 1:1:2 | " | Yes, c | b | 56 | 51 |
| 4 | Co$_2$(CO)$_8$—Ru$_3$(CO)$_{12}$—DIPY | 1:1:3 | " | Yes | b | 69 | 57 |
| 5 | Co$_2$(CO)$_8$—Ru$_3$(CO)$_{12}$—DIPY | 1:1:2 | " | Yes, c | b, d | 74 | 66 |
| 6 | Co$_2$(CO)$_8$—Ru$_3$(CO)$_{12}$—PHEN | " | " | Yes | b | 38 | 29 |
| 7 | Co$_2$(CO)$_8$—Ru$_3$(CO)$_{12}$—TPTZ | 1:1:e, f | " | Yes, c | b | 71 | 57 |
| 8 | Co$_2$(CO)$_8$—Ru$_3$(CO)$_{12}$—TPTZ | 1:1:e | 1,4-dioxane | Yes | b | 76 | 59 |
| 9 | Co$_2$(CO)$_8$—Ru$_3$(CO)$_{12}$—DIPY, g | 1:1:2 | 1,3-dioxolane | Yes, c | b | 70 | 53 |
| 10 | Co$_2$(CO)$_8$—Ru$_3$(CO)$_{12}$—DIPY, h | " | " | Yes, c | b | 69 | 56 |
| 11 | Co$_2$(CO)$_8$—RuO$_2$—DIPY | " | " | Yes, c | b | 70 | 55 |
| 12 | Co$_2$(CO)$_8$—10% Ru/C—DIPY | " | " | Yes, c | b | 71 | 55 | a Run conditions: 90° C., 1800 psi (12,410 kPa), ½ (CO/H$_2$)
b Run conditions: 90° C., 2000 psi (13,790 kPa), ¼ (CO/H$_2$)
c Double promoter concentration
d Scale-up run, made in 300 cc capacity batch reactor, four ethylene oxide additions
e Ratio is 1:1:1, Co:Ru:TPTZ
f Double catalyst concentration
g DIPY from Zeneca Corp.
h DIPY from Zeneca, recrystallized from hexane

TABLE 2

| EXP. | CATALYST COMPOSITION | Co:Ru:N | SOLVENT | $Me_2C_{12}N$ | CONDITIONS | PDO SEL. (%) | PDO YIELD (mole %) |
|---|---|---|---|---|---|---|---|
| 5 | $Co_2(CO)_8$—$Ru_3(CO)_{12}$—DIPY | 1:1:2 | 1,3-dioxolane | Yes | a | 74 | 66 |
| 13 | $Co_2(CO)_8$—$Ru_3(CO)_{12}$—DIPY, b | " | 1,3-dioxane, c | Yes | a | 67 | 54 |
| 14 | $Co_2(CO)_8$—$Ru_3(CO)_{12}$—DIPY, b | " | 1,3-dioxane, c, d | Yes | a | 72 | 63 |
| 15 | $Co_2(CO)_8$—$Ru_3(CO)_{12}$—DIPY, b | " | 1,4-dioxane | Yes | a | 71 | 47 |
| 16 | $Co_2(CO)_8$—$Ru_3(CO)_{12}$—DIPY | " | 2-ethyl-2-methyl-1,3-dioxolane | Yes | e | 54–73, f | 58 |
| 17 | $Co_2(CO)_8$—$Ru_3(CO)_{12}$—DIPY | " | MTBE | Yes | a | 36 | 21 |
| 18 | $Co_2(CO)_8$—$Ru_3(CO)_{12}$—DIPY | 2:1:2 | THF | Yes | g | N.D. | 4.5 |
| 19 | $Co_2(CO)_8$—$Ru_3(CO)_{12}$—DIPY | 1:1:2 | N-($Me_2$-N-ethyl)-morpholine | Yes | a | N.D. | <1 |
| 20 | $Co_2(CO)_8$—$Ru_3(CO)_{12}$—DIPY | " | Sulfolane | Yes | a | 37 | 14 | a Run conditions: 90° C., 2000 psi (13,790 kPa), ¼ (CO/$H_2$)
b Catalyst concentration increased by 1.5
c 1,3-Dioxane from Ferro Corporation
d Larger batch, 99.8% purity
e Run conditions: 100° C., 2000 psi (13,790 kPa), ¼ (CO/$H_2$)
f Two-phase product liquid, PDO concentrated in the heavier phase
g Run conditions: 90° C., 1500 psi (10,340 kPa), ½ (CO/$H_2$)

EXAMPLE 21

In Example 21 a typical life study of the catalyst complex was conducted. Dicobalt octacarbonyl-triruthenium dodecacarbonyl-2,2'-dipyridyl catalyst solubilized in 1,3-dioxolane was used as the catalyst precursor for eighteen EO additions and four PDO distillations. Here the initial Co—Ru-DIPY stoichiometry was 1:1:1 and each EO hydroformylation was conducted at 90° C. under 2000 psi (13,790 kPa) of ¼ (CO/$H_2$) syngas. The typical operating procedures are as follows:

1. Four EO additions to the Co—Ru—N-heterocyclic catalyst solubilized in a cyclic ether solvent, with hydroformylation/hydrogenation of each EO addition to PDO as detailed previously.
2. PDO recovery by vacuum distillation after solvent stripping.
3. Recycle of the bottoms Co—Ru—N-heterocyclic catalyst solution in PDO, with fresh ether solvent. Data are given in Table 3:

TABLE 3

| # EO Additions | PDO Yield (mole %) | PDO Sel. (%) | PDO/EtOH | Distilled PDO (gm) |
|---|---|---|---|---|
| 4 | 66 | 74 | 5.0 | 15 |
| 4 | 49 | 73 | 6.8 | 38 |
| 4 | 52 | 67 | 7.9 | 49 |
| 4 | 69 | 57 | 5.8 | 31 |
| 2 | 52 | 44 | 11.3 | N.D. |

Generally, we have found that as the number of cycles increases there is a slow build-up of organic heavies, particularly 3-hydroxypropyl-2-hydroxyethyl ether, 3-hydroxypropyl 3-hydroxypropionate, and the PDO/EG esters of 3-hydroxypropionate (identified by GC-ms/IR). With constant liquid sampling, we are also depleting the system of catalyst, so that the time to complete each EO uptake is stretched from 4 to 9 hours. All product solutions exhibit very little residual HPA (<1%) and acetaldehyde exit concentrations never rise above 0.4%. After 18 EO additions the final product is a clear, deep red liquid, with no evidence of precipitates. Cobalt and ruthenium recoveries are 68% and 64%, respectively, basis metals analyses (X-ray florescence). Likewise, inspecting the reactor after 5 weeks of operation, it is clean, with no residual solid.

EXAMPLE 22

Figure 5:
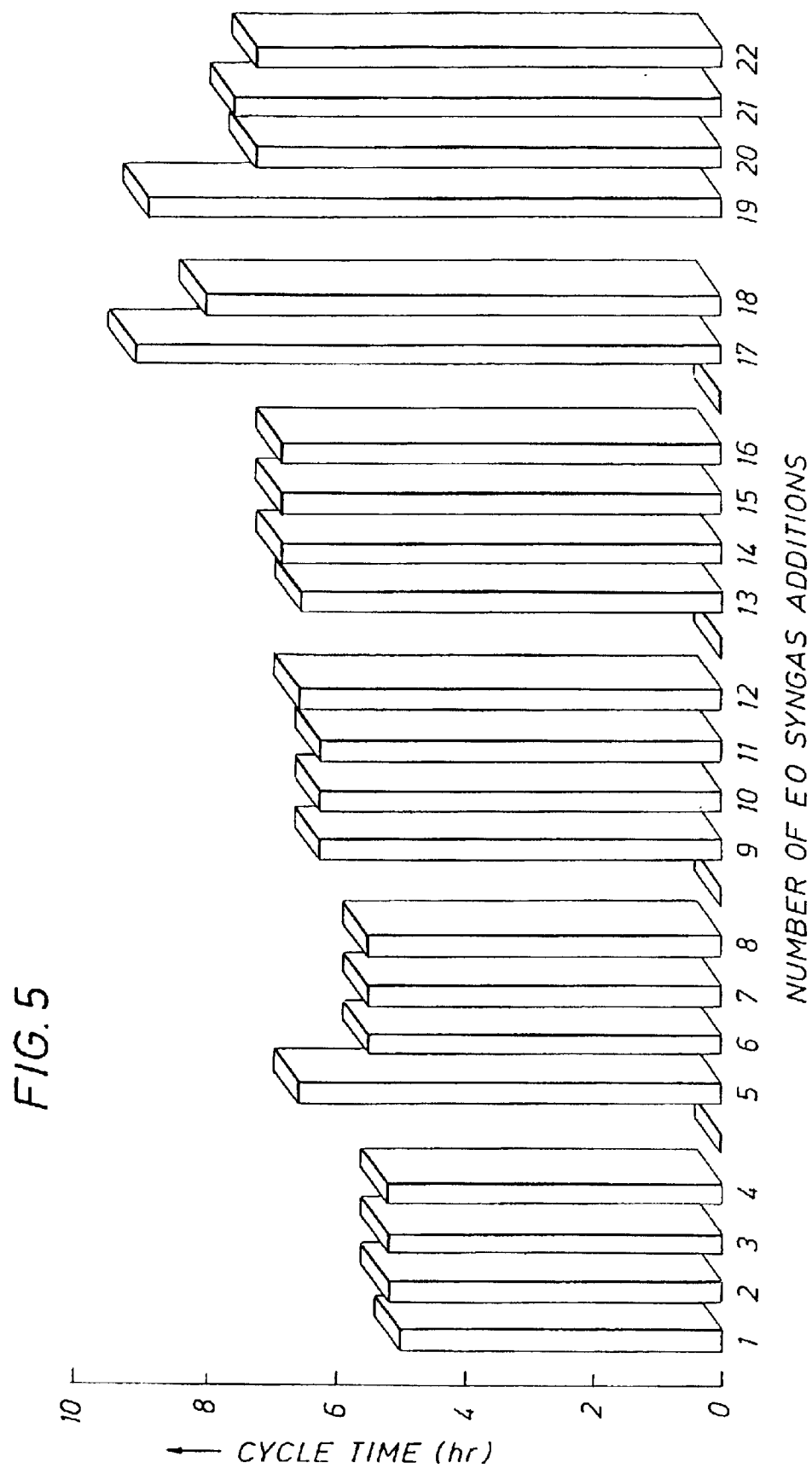
FIG. 5 is a bar graph showing EO uptake times for the cobalt-ruthenium-2,2'-dipyridyl catalyst, solubilized in 1,3-dioxolane, when used for 1,3-propanediol one-step syntheses.

An experimental series very similar to that of Example 21 was also performed where the intermediate solids formed during the multi-cycling process were removed by filtration (prior to PDO distillation) and after 18 EO additions a small quantity of make-up catalyst was added. An additional four EO additions were completed, making a grand total of 22. EO uptake times for this second catalyst life study are illustrated in FIG. 5.

EXAMPLES 23–98

A series of cobalt-ruthenium homogeneous catalysts in association with a number of N-heterocyclic ligands were employed for one-step 1,3-PDO synthesis, using different molar ratios of components of catalyst complex, various solvents, and a range of reaction conditions. These runs were conducted in 100 cc capacity batch reactors, hooked to a synthesis gas manifold, and having the appropriate temperature/pressure readouts and controls. These data illustrate the use of:

A series of N-heterocyclic ligands including 2,2'-bipyrimidine (BPYM), 2,2'-dipyridyl (DIPY), 2,4,6-tripyridyl-s-triazine (TPTZ), 1,10-phenanthroline, 2,2'-biquinoline, 2,2'-dipyridylamine, di-2-pyridyl ketone, 4,7-dimethylphenanthroline, 5,6-dimethylphenanthroline, pyrimidine, pyridazine, quinazoline, neocuproine, 3,6-di-2-pyridyl-1,2,4,5-tetrazine, 2,2':6',2''-terpyridine, and 3-(2-pyridyl)-5,6-diphenyl-1,2,4-triazine.

A series of ruthenium precursors including triruthenium dodecacarbonyl, ruthenium(IV) oxide, and 10% ruthenium-on-carbon.

A range of ether solvents including MTBE, tetrahydrofuran (THF), 1,3-dioxolane, 1,4-dioxolane, dimethyl-1,3-dioxolane, 4-methyl-1,3-dioxolane, 2-ethyl-2-methyl-dioxolane, and 1,4-dioxane.

Promoters including triethylamine and N,N-dimethyldodecylamine, as well as sodium acetate.

Experimental data are summarized in the following Tables 4–19 for this direct, one-step, conversion of ethylene oxide plus synthesis gas to 1,3-propanediol. In the Product Phases column, T is the top phase, B is the bottom phase, and P is the total product when only one phase is present.

TABLE 4

| EXP. | Catalyst | Solvent | Temp °C. | Time EO Uptake (hrs) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 23 | Co$_2$(CO)$_8$—Ru(CO)$_{12}$ BPYM | MTBE | 90 | 3 | T<br>B<br>W/W | 18.3<br>1.2 | 1.4$^{d,e}$<br>32.2$^e$<br>4.5 | 0.1$^e$<br>0.7$^e$<br>0.2 | 4.6<br>2.7<br>3.0 | 26<br>48 | 13 |
| 24 | Co$_2$(CO)$_8$—Ru(CO)$_{12}$BPYM | MTBE | 80 | 3.5$^a$ | P$^c$<br>W/W | 19.0 | 1.0<br>2.3 | 0.4<br>1.0 | 10.3<br>4.0<br>1.5 | N.D. | 6.4 |
| 25 | Co$_2$(CO)$_8$—Ru(CO)$_{12}$BPYM$^b$ | MTBE | 90 | 2.5 | P<br>W/W | 18.9 | 1.1<br>3.7 | 1.0<br>2.0 | 5.5<br>4.4<br>2.6 | N.D. | 8.3 |
| 26 | [Ru$_2$(CO)$_4$(MeCOO) (BPYM)$_2$]$^{+f}$ | MTBE | 80 | 4$^a$ | P$^g$<br>W/W | 18.7 | 0.3<br>N.D. | 0.1<br>N.D. | 7.0<br>0.9<br>N.D. | N.D. | 1.1 |
| 27 | Ru$_3$(CO)$_{12}$-BPYM | Tol/ClC$_6$H$_5$ | 90 | 1.75$^a$ | P<br>W/W$^j$ | 23.2 | 0.2<br>5.1$^d$ | N.D.<br>N.D. | 0.9<br>0<br>3.9 | N.D. | 4.8 |
| 28 | [Ru$_2$(CO)$_4$(MeCOO) (BPYM)$_2$]$^{+b,h}$ | MTBE | 90 | 2$^a$ | P<br>W/W | 18.5 | 1.2<br>N.D. | 0.1<br>N.D. | 3.9<br>4.3<br>N.D.<br>4.3 | N.D. | 5.4 |

$^a$Run with ½ (CO/H2) gas
$^b$Run with no NaOAc promoter
$^c$Some heavy catalyst residue in bottom of reactor
$^d$Checked by PDO spiking
$^e$Confirmed by GC-ms/IR
$^f$Product 24090-119
$^g$Large quantity of catalyst residue
$^h$Product 24090-135
$^i$Lot of solids in water wash

TABLE 5

| EXP. | Catalyst | Solvent | Temp °C. | Time EO Uptake (hrs) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 29 | Co$_2$(CO)$_8$—Ru$_3$(CO)$_{12}$BPYM | THF | 90 | 4$^a$ | P<br>W/W | 23.2 | 2.8<br>N.D. | 0.1<br>N.D. | 12.5<br>N.D.<br>12.5 | 45 | 15 |

TABLE 5-continued

| EXP. | Catalyst | Solvent | Temp ° C. | Time EO Uptake (hrs) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 30 | Co$_2$(CO)$_8$—Ru$_3$(CO)$_{12}$BPYM[d] | 1,3-dioxolane | 90 | 3[a] | P W/W[c] | 27.1 | 5.8 N.D. | 0.3 N.D. | 21.7 N.D. | 51 | 29 |
| 31 | Co$_2$(CO)$_8$—Ru$_3$CO)$_{12}$BPYM | THF | 90 | 1.5[a,b] | P W/W | 22.3 | N.D. N.D. | 1.0 N.D. | 21.7 N.D. | N.D. | <0.1 |
| 32 | 2[Co$_2$(CO)$_8$—Ru$_3$(CO)$_{12}$BPYM] | 1,3-dioxolane | 90 | 2.5[a] | P W/W | 29.1 | N.D.[f] N.D. | 1.2 N.D. | N.D. N.D. | N.D. | <0.1[f] |
| 33 | Co$_2$(CO)$_8$—Ru$_3$(CO)$_{12}$BPYM | 1,4-dioxolane | 90 | 1.75[a] | P W/W | 26.7 | 0.2 N.D. | [e] [e] | N.D. 1.1 N.D. | N.D. | 1.3 |
| 34 | Co$_2$(CO)$_8$—Ru$_3$(CO)$_{12}$BPYMMe$_2$C$_{12}$H$_{25}$N | 1,3-dioxolane | 90 | 3.25[a] | P W/W | 27.5 | 5.6 N.D. | 1.0 N.D. | 1.1 23.0 N.D. 23.0 | 51 | 29 |

[a]Run with ½ (CO/H2) gas
[b]Half the usual EO charge
[c]Small quantity of suspension in water wash
[d]New batch of 2,2-bipyrimidine
[e]Could not be determined, HPA and 1,4-dioxane have the same glc retention time
[f]Repeat run −185R gave very similar data

TABLE 6

| EXP. | Catalyst | Solvent | Temp ° C. | Time EO Uptake (hrs) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 35 | CO$_2$(CO)$_8$—Ru$_3$(CO)$_{12}$BPYM[a] | THF | 90 | 3[b] | P W/W | 23.5 | 2.4 N.D. | 1.1[e] N.D. | 9.9 N.D. | 30 | 12[e] |
| 36 | CO$_2$(CO)$_8$—2[Ru$_3$(CO)$_{12}$BPYM] | 1,3-dioxolane | 90 | 2.5[b] | P W/W | 28.0 | 2.1 N.D. | 3.7 N.D. | 9.9 8.5 N.D. | 22 | 11 |
| 37 | 2[Co$_2$(CO)$_8$—Ru$_3$(CO)$_{12}$BPYM][c] | 1,3-dioxolane | 90 | 2.5[b] | P W/W | 52.2 | N.D. N.D. | 1.3 N.D. | 8.5 N.D. N.D. | N.D. | <0.1 |
| 38 | Co$_2$(CO)$_8$—Ru$_3$(CO)$_{12}$BPYM[d] | 1,3-dioxolane | 90 | 3[b] | P W/W | 28.0 | 6.9 N.D. | 0.4 N.D. | N.D. 26.7 N.D. | 57 | 36 |
| 39 | Co$_2$(CO)$_8$—Ru$_3$(CO)$_{12}$BPYMMe$_2$C$_{12}$H$_{25}$N | 1,3-dioxolane[f] | 90 | 3.5[b] | P W/W | 27.9 | 7.1 N.D. | 0.3 N.D. | 26.7 27.7 N.D. | 61 | 34 |
| 40 | Co$_2$(CO)$_8$—Ru$_3$(CO)$_{12}$BPYM[d,g] | 1,3-dioxolane | 90 | 2.75[b] | P[h] W/W | 27.9 | 4.1 N.D. | 2.4 N.D. | 27.7 16.6 N.D. 16.6 | 36 | 20 |

[a]A repeat of Run 24090-143, using new batch of BPYM (#2)
[b]Run with ½ (CO/H$_2$) gas
[c]Double 1,3-dioxolane solvent also
[d]No promoter
[e]More HPA, CH$_3$CHO, C2H5CHO and acrolein, less EtOH, in −191 versus −143
[f]Crude (99%) 1,3-dioxolane solvent
[g]BPYM sample 23768-45
[h]Some precipitated solids in product phase

TABLE 7

| EXP. | Catalyst | Solvent | Temp °C. | Time EO Uptake (hrs) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 41 | Co$_2$(CO)$_8$—Ru$_3$(CO)$_{12}$BPYM[a] | 1,3-dioxolane | 90[b] | 4 | P[c] W/W | 27.9 | 7.9 N.D. | 0.3 N.D. | 31.0 N.D. | 64 | 38 |
| 42 | Co$_2$(CO)$_8$—Ru$_3$(CO)$_{12}$BPYM[a] | 1,3-dioxolane[d] | 90[b] | 4.25 | P W/W | 27.5 | 8.0 N.D. | 0.2 N.D. | 31.0 32.5 N.D. | 67 | 41 |
| 43 | Co$_2$(CO)$_8$—Ru$_3$(CO)$_{12}$BPYM[a] | 1,3-dioxolane | 90[e] | 4.5 | P[c] W/W | 28.7 | 10.4 N.D. | 0.4 N.D. | 32.5 39.4 N.D. | 61 | 49 |
| 44 | Co$_2$(CO)$_8$—Ru$_3$(CO)$_{12}$BPYM[f] | Me$_2$-1,3-Dioxolane | 90 | 3.5 | P[c] W/W | 23.9 | 5.9 4.6 | [g] [g] | 39.4 23.8 4.0 | 58[g] | 36 |
| 45 | Co$_2$(CO)$_8$—Ru$_3$(CO)$_{12}$BPYM[f] | 4-Me-1,3 dioxolane | 90 | 3.5 | P W/W | 25.1 | 5.5 N.D. | N.D. N.D. | 27.8 21.8 N.D. | 44 | 26 |
| 46 | Co$_2$(CO)$_8$—Ru$_3$(CO)$_{12}$BPYM[f] | 2-Me-1,3-dioxolane | 90 | 4 | P W/W | 26.3 | 6.9 0.4 | 1.2 N.D. | 21.8 24.4 0.3 | 47 | 29 |
| 47 | Co$_2$(CO)$_8$—Ru$_3$(CO)$_{12}$BPYM[f] | Propylene Carbonate | 90 | 1.25[h] | P W/W | 29.4 | <0.1 N.D | 0.8 N.D. | 24.7 N.D. N.D. N.D. | N.D. | <0.1 |

[a]No promoter
[b]Run at 1800 psi (12,410 kPa) with ¼ (CO/H$_2$) syngas
[c]Some precipitated solids in product phase
[d]Crude (99%) 1,3-dioxolane solvent
[e]Run at 1800 psi (12,410 kPa) with ½ (CO/H$_2$) syngas
[f]Added Et$_3$N promoter
[g]HPA eluted on GC with solvent
[h]Stirrer belt broke during catalyst preparation step

TABLE 8

| EXP. | Catalyst | Solvent | Temp °C. | Time EO Uptake (hrs) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 48 | Co$_2$(CO)$_8$—Ru$_3$(CO)$_{12}$BPYM[a] | 1,3-dioxolane | 90[b] | 4 | P[c] W/W | 28.1 | 9.5 N.D. | 0.3 N.D. | 37.3 N.D. | 65 | 47 |
| 49 | 2[Co$_2$(CO)$_8$—Ru$_3$(CO)$_{12}$BPYM][a] | " | 90 | 2.5 | P[c] W/W | 28.4 | 6.4 N.D. | 1.5 N.D. | 37.3 27.5 N.D. | 43 | 34 |
| 50 | Co$_2$(CO)$_8$—Ru$_3$(CO)$_{12}$BPYM[a,d] | " | 90[e] | 4.5 | P[c] W/W | 28.2 | 8.9 N.D. | 0.4 N.D. | 27.5 36.1 N.D. | 63 | 43 |
| 51 | Co$_2$(CO)$_8$—Ru$_3$(CO)$_{12}$BPYM[a] | " | 90[f] | 3.75 | P[c] W/W | 28.3 | 10.4 N.D. | 0.2 N.D. | 36.1 40.2 N.D. 40.2 | 59 | 49 |

[a]No promoter
[b]Run at 2000 psi (13,790 kPa) with ¼ (CO/H$_2$) syngas
[c]Some precipitated solids in product phase
[d]Using new batch of BPYM (#3)
[e]Run at 1800 psi (12,410 kPa) with ½ (CO/H$_2$) syngas
[f]Run at 2000 psi (13,790 kPa) with ½ (CO/H$_2$) syngas

TABLE 9

| EXP. | Catalyst | Solvent | Temp °C. | Time EO Uptake (hrs) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 52 | $Co_2(CO)_8$—2[$Ru_3(CO)_{12}$DIPY][a] | 1,3-dioxolane | 90[b] | 3.25 | P W/W | 28.9 | 5.0 N.D. | 4.2 N.D. | 20.3 N.D. | 31 | 25 |
| 53 | $Co_2(CO)_8$—2[$Ru_3(CO)_{12}$DIPY]$Me_2C_{12}H_{25}N$ | 1,3-dioxolane | 90[b] | 4 | P[c] W/W[c] | 29.0 | 11.3 N.D. | 4.1 N.D. | 20.3 46.0 N.D. 46.0 | 57 | 54[d] |

[a]No promoter
[b]Run at 2000 psi (13,790 kPa) with ¼ (CO/H$_2$) syngas
[c]Black solids in reactor and water wash
[d]Approximate PDO + HPA yield: 74%

TABLE 10

| EXP. | Catalyst | Solvent | Temp °C. | Time EO Uptake (hrs) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 54 | $Co_2(CO)_8$—$Ru_3(CO)_{12}$-1/2 TPTZ | MTBE | 90[b] | 2 | P W/W | 18.7 | 0.2 0.5 | 0.5 N.D. | 0.8 0.3 | N.D. | 1.3 |
| 55 | $Co_2(CO)_8$—2[$Ru_3(CO)_{12}$-TPTZ][a] | 1,3-dioxolane | 90[b] | 4.75 | P W/W | 29.1 | 10.6[i] N.D. | N.D. N.D. | 1.1 44.0 N.D. | 79 | 51 |
| 56 | $Co_2(CO)_8$—2[$Ru_3(CO)_{12}$-TPTZ][c] | " | 90[b] | >3 | P W/W[f] | 27.4 | 2.15 0.2 | 0.3 <0.1 | 44.0 4.6 0.2 | 61 | 5.7[e] |
| 57 | $Co_2(CO)_8$—2[$Ru_3(CO)_{12}$-TPTZ][d] | " | 90[b] | 4 | P W/W | 27.7 | 4.0 0.3 | 0.1 N.D. | 4.8[e] 13.8 0.2 | 67 | 19[e] |
| 58 | $Co_2(CO)_8$—2[$Ru_3(CO)_{12}$-TPTZ][a] | " | 90[b] | G | P W/W | 26.9 | 4.0[h] | <0.1[h] | 14.0[e] 12.6[h] | 73 | 23[e] |
| 59 | 11/2[$Co_2(CO)_8$—2{$Ru_3(CO)_{12}$-TPTZ}][a] | " | 90[b] | 4.75 | P W/W | 28.4 | 9.8 1.1 | 0.1 N.D. | 12.6[e] 34.3 0.7 | 76 | 45[e] |
| 60 | $Co_2(CO)_8$—2[$Ru_3(CO)_{12}$3/4TPTZ][a] | " | 90[b] | 5.25 | P W/W | 28.2 | 12.9 1.5 | 0.1 N.D. | 35.0 40.6 1.0 41.6 | 80 | 54[e] |

[a]Co-Ru-Ligand pretreatment at 90° C.
[b]Run at 2000 psi (13,790 kPa) with ¼ (CO/H$_2$) syngas
[c]Co-Ru-Ligand pretreatment at 130° C.
[d]Co-Ru-Ligand pretreatment at 110° C.
[e]New glc column and new PDO response factor
[f]Some solids in water wash phase
[g]A repeat of Run 24285-117 in ir cell
[h]No water wash in this run
[i]Confirmed by gc-ir/ms, plus ethanol, 1-propanol, 3-(2-hydroxyethoxy)-1-propanol, (3-hydroxypropyl)-3-hydroxypopionate

TABLE 11

| EXP. | Catalyst | Solvent | Temp °C. | Time EO Uptake (hrs) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 61 | $Co_2(CO)_8$—$2[Ru_3(CO)_{12}$-3/4 TPTZ$]^a$ | 1,3-dioxolane | 90[b] | 5.25 | P W/W | 26.9 | 5.5 0.7 | N.D. N.D. | 22.7 0.5 | 73 | 29[c] |
| 62 | $Co_2(CO)_8$—$2[Ru_3(CO)_{12}$-3/4TPTZ$]^a$ | 1,4-dioxane | 90[b] | 5.5 | P W/W | 28.5 | 13.9 1.7 | 0.1 N.D. | 23.2 47.5 1.2 | 76 | 59[c] |
| 63 | $2\{Co_2(CO)_8$—$2\{Ru_3(CO)_{12}$-TPTZ$\}]^a$ | 1,3-dioxolane | 90[b] | 5.5 | P W/W[e] | 29.9 | 11.6 1.1 | 0.1 N.D. | 48.7 45.9 0.8 | 71 | 57[c] |
| 64 | $Co_2(CO)_8$—$2[Ru_3(CO)_{12}$-1/2TPTZ$]^a$ | " | 90[b] | 5.25 | P W/W | 28.5 | 12.7 1.4 | 0.3 N.D. | 46.7 40.7 1.0 | 78 | 52[c] |
| 65 | $Co_2(CO)_8$—$2[Ru_3(CO)_{12}$-3/4TPTZ$]^a$ | 2-Et-2-Me-Dioxolane | 90[b] | 6.5 | P[h] W/W | 24.8 | 5.8 8.1 | 0.4 N.D. | 41.7 22.6 5.7 | 66 | 35 |
| 66 | $2[Co_2(CO)_8$—$2\{Ru_3(CO)_{12}$-TPTZ$\}]^a$ | 1,3-dioxolane | 90[b] | F | P W/W | f | 4.3[g] | 0.5[g] | 28.3 14.0[g] | 61 | 29 |
| 67 | $3/4[Co_2(CO)_8$—$2\{Ru_3(CO)_{12}$3/4TPTZ$\}]^a$ | 1,4-dioxane | 90[b] | 6 | P W/W | 27.8 | 10.6 1.0 | N.D. N.D. | 14.0 39.5 0.8 40.3 | 66 | 47 |

[a] Co-Ru-Ligand pretreatment at 90° C.
[b] Run at 2000 psi (13,790 kpa) with ¼ (CO/H$_2$) syngas
[c] New glc column and new PDO response factor
[d] A repeat run, very similar results
[e] Small amount of solids in water wash
f A repeat of run 24285-167 in ir cell
[g] No water wash in this run
[h] Some solids in the reactor

TABLE 12

| EXP. | Catalyst | Solvent | Temp °C. | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|
| 68 | $Co_2(CO)_8$—$[Ru_2(CO)_4$(MeCOO)(1,10-PHEN)$_2]^{+a}$ | MTBE | 80[c] | P W/W | 19.1 | 0.3 2.4 | 3.7 17.0 | 1.3 2.0 | N.D. | 3.7 |
| 69 | $Co_2(CO)_8$—$[Ru_2(CO)_4$(MeCOO)(1,10-PHEN)$_2]^{+b}$ | " | 80[c] | P W/W | 18.2 | 0.4 2.6 | 3.2 17.3 | 3.3 1.3 2.3 | N.D. | 4.3 |
| 70 | $Co_2(CO)_8$—$[Ru_2(CO)_4$(MeCOO)(1,10-PHEN)$_2]^{+d}$ | " | 80[c] | P W/W | 18.4 | 0.3 0.4 | 5.0 9.1 | 3.6 1.5 0.4 | N.D. | 2.1 |
| 71 | $Co_2(CO)_8$—$Ru_3(CO)_{12}$-½ Bipyrimidine | " | 90 | T B W/W | 18.3 1.2 | 1.4[e] 32.2 4.5 | 0.1 0.7 0.2 | 1.9 4.6 2.7 3.0 | 26 48 | 13 |
| 72 | $Co_2(CO)_8$—$Ru_3(CO)_{12}$-½ Dipyridyl | " | 90[c] | P W/W | 19.1 | 1.1 2.8 | 0.1 0.2 | 10.3 4.4 1.7 6.1 | 29 | 7.3 |

TABLE 12-continued

| EXP. | Catalyst | Solvent | Temp °C. | Product Phases | wt(g) | Conc. (%) PDO | HPA | PDO Production (mmole) | PDO Sel. (%) | PDO Yield (mole %) |
|---|---|---|---|---|---|---|---|---|---|---|
| 73 | Co$_2$(CO)$_8$—Ru$_3$(CO)$_{12}$-½ Biquinoline | " | 90$^c$ | P$^{f,g}$ W/W | 19.5 | 0.3$^e$ 1.0 | 0.6 3.4 | 1.2 0.8 ——— 2.0 | N.D. | 1.8 |

$^a$Product 24090-75A, made at 70° C.
$^b$Product 24090-75B, made at 30° C.
$^c$Run with ½ (CO/H$_2$) gas
$^d$Product 24090-93
$^e$Checked by PDO spiking
$^f$Some black precipitate in liquid product mix
$^g$Larger EO addition than usual

TABLE 13

| EXP. | Catalyst | Solvent | Temp °C. | Product Phases | wt(g) | Conc. (%) PDO | HPA | PDO Production (mmole) | PDO Sel. (%) | PDO Yield (mole %) |
|---|---|---|---|---|---|---|---|---|---|---|
| 74 | Co$_2$(CO)$_8$—Ru$_3$(CO)$_{12}$-1/2 4,4' Me$_2$-2,2'-Dipyridyl | MTBE | 90$^a$ | P$^c$ W/W | 19.2 | 1.4 1.4 | 0.1 0.2. | 5.3 0.9 ——— 6.2 | N.D. | 7.6 |
| 75 | Co$_2$(CO)$_8$—Ru$_3$(CO)$_{12}$-1/2 2,2'-Dipyridylamine | " | 90$^a$ | P$^b$ W/W | 19.0 | 0.2 N.D. | 0.6 N.D. | 0.6 N.D. ——— 0.6 | N.D. | 0.7 |
| 76 | Co$_2$(CO)$_8$—Ru$_3$(CO)$_{12}$-½ Di-2-pyridylketone | " | 90$^a$ | P$^b$ W/W | 18.6 | <0.1 N.D. | 0.6 N.D. | 0.4 N.D. ——— 0.4 | N.D. | 0.5 |
| 77 | Co$_2$(CO)$_8$—Ru$_3$(CO)$_{12}$-½ 1,10-PHEN | " | 90$^a$ | P W/W(T) W/W(B)$^d$ | 19.0 | 0.9 2.6 3.1 | 0.3 0.9 1.2 | 3.8 1.5 0.4 ——— 5.7 | N.D. | 6.8 |
| 78 | Co$_2$(CO)$_8$—Ru$_3$(CO)$_{12}$-½ 4,7-Me$_2$PHEN | " | 90$^a$ | P W/W$^d$ | 19.1 | 1.1 2.7 | 0.1 0.1. | 3.8 1.9 ——— 5.7 | N.D. | 6.8 |
| 79 | Co$_2$(CO)$_8$—Ru$_3$(CO)$_{12}$-½ 5,6-Me$_2$PHEN | " | 90$^a$ | P W/W$^d$ | 19.0 | 0.9 4.6 | <0.1 0.2 | 3.3 3.1 ——— 6.4 | N.D. | 7.8 |
| 80 | Co$_2$(CO)$_8$—Ru$_3$(CO)$_{12}$- Pyrimidine | " | 90$^a$ | P W/W$^d$ | 18.7 | 0.2 0.6 | 0.9 2.0. | 0.9 0.4 ——— 1.3 | N.D. | 1.6 |

$^a$Run with ½ (CO/H$_2$) gas
$^b$Considerable black precipitate in reactor at end of run
$^c$Considerable hard reddish precipitate in reactor at end of run
$^d$Solid suspension in this water wash phase

TABLE 14

| EXP. | Catalyst | Solvent | Temp °C. | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|
| 81 | Co$_2$(CO)$_8$-Ru$_3$(CO)$_{12}$-Pyridazine | MTBE | 90$^a$ | P W/W$^b$ | 19.0 | 0.2 0.5 | 0.9 2.2 | 0.8 0.4 | N.D. | 1.3 |
| 82 | Co$_2$(CO)$_8$-Ru$_3$(CO)$_{12}$-Quinazoline | " | 90$^a$ | P W/W$^b$ | 18.4 | 0.2 0.9 | 0.8 2.7 | 1.2 0.8 0.7 | N.D. | 1.9 |
| 83 | Co$_2$(CO)$_8$-Ru$_3$(CO)$_{12}$-½ Neocuproine | " | 90$^a$ | P W/W$^b$ | 18.6 | 0.2 0.6 | 0.4 1.1 | 1.5 1.0 0.5 | N.D. | 1.8 |
| 84 | Co$_2$(CO)$_8$-Ru$_3$(CO)$_{12}$-½ 2,2'-Dipyridylamine | THF | 100$^{a,c}$ | P W/W$^d$ | 21.3 | 0.1 N.D. | 1.4 N.D. | 1.5 0.6 N.D. | N.D. | 1.3 |
| 85 | Co$_2$(CO)$_8$-Ru$_3$(CO)$_{12}$-¼ 3,6-Dipyridyltetrazine | MTBE | 90$^a$ | P$^e$ W/W$^b$ | 18.5 | 0.2 2.6 | 1.1 1.1 | 0.6 0.9 1.1 | N.D. | 2.3 |
| 86 | Co$_2$(CO)$_8$-Ru$_3$(CO)$_{12}$-¼ 2,4,6-Tripyridyl-S-Triazine | " | 90$^a$ | P W/W$^b$ | 18.7 | 0.2 0.5 | 0.5 N.D. | 2.0 0.8 0.3 | N.D. | 1.3 |
| 87 | Co$_2$(CO)$_8$-Ru$_3$(CO)$_{12}$-½ 2,2:6,2-Terpyridine | " | 90$^a$ | P$^e$ W/W$^b$ | 19.5 | 0.1 N.D. | 2.1 N.D. | 1.1 0.5 N.D. 0.5 | N.D. | 0.6 |

$^a$Run with ½(CO/H$_2$) gas
$^b$Solid suspension in water wash phase
$^c$Half the usual EO charge
$^d$Small amount of solids in water wash phase
$^e$Some solids in product phase

TABLE 15

| EXP. | Catalyst | Solvent | Temp °C. | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|
| 88 | Co$_2$(CO)$_8$—Ru$_3$(CO)$_{12}$-½ 3,6-Dipyridyltetrazine | THF | 90$^a$ | P W/W$^b$ | 22.9 | 0.2 N.D. | 0.5 N.D. | 0.8 N.D. | N.D. | 1.0 |
| 89 | Co$_2$(CO)$_8$—Ru$_3$(CO)$_{12}$-½ 2,3-Bis(Pyridyl)pyrazine | MTBE | 90$^a$ | P$^c$ W/W$^b$ | 18.8 | 0.1 N.D. | 1.0 N.D. | 0.8 0.5 N.D. | N.D. | 0.6 |
| 90 | 2[Co$_2$(CO)$_8$—Ru$_3$(CO)$_{12}$]-½ 3,6-Dipyridyltetrazine | THF | 90$^a$ | P W/W | 23.9 | 0.1 N.D. | N.D. N.D. | 0.5 0.4 N.D | N.D. | 0.5 |
| 91 | Co$_2$(CO)$_{12}$Ru$_3$(CO)$_{12}$-½ 3-Pyridyl-5,6-diphenyl triazine$^d$ | MTBE | 90$^a$ | P W/W$^b$ | 19.6 | 0.3 N.D. | 0.5 N.D. | 0.4 1.1 N.D. 1.1 | N.D. | 1.3 |

$^a$Run with ½ (CO/H$_2$) gas
$^b$Solid suspension in water wash phase
$^c$Some solids in product phase
$^d$Catalyst prep 3 days before run

TABLE 16

| EXP. | Catalyst | Solvent | Temp °C. | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|
| 92 | $Co_2(CO)_8$—$Ru_3(CO)_{12}$-3,6-Dipyridyl-tetrazine | MTBE | 90 | P<br>W/W | 18.5 | 0.2<br>1.6 | 1.1<br>2.6 | 0.9<br>1.1 | N.D. | 2.3 |
| 93 | $Co_2(CO)_8$—$Ru_3(CO)_{12}$-2,2:6,2-Terpyridine | " | 90 | P<br>W/W | 19.5 | 0.1<br>N.D. | 2.1<br>N.D. | 2.0<br>0.5<br>N.D. | N.D. | 0.6 |
| 94 | $Co_2(CO)_8$—$Ru_3(CO)_{12}$-3,6-Dipyridyl-tetrazine | THF | 90 | P<br>W/W | 22.9 | 0.2<br>N.D. | 0.5<br>N.D. | 0.5<br>0.8<br>N.D. | N.D. | 1.0 |
| 95 | $Co_2(CO)_8$—$Ru_3(CO)_{12}$-3-(2-Pyridyl)-5,6-Diphenyl 1,2,4-Triazine | MTBE | 90 | P<br>W/W | 19.6 | 0.3<br>N.D. | 0.5<br>N.D. | 0.8<br>1.1<br>N.D. | N.D. | 1.3 |
| 96 | $Co_2(CO)_8$—$Ru_3(CO)_{12}$-3,6-Dipyridyl-tetrazine | 1,3-dioxolane | 90 | P<br>W/W | 27.7 | 3.7<br>N.D. | 1.7<br>N.D. | 1.1<br>14.7<br>N.D. | N.D. | 18 |
| 97 | $Co_2(CO)_8$—$Ru_3(CO)_{12}$-3-Pyridyl-5,6-Diphenyl Triazine Disulfonic acid salt | 1,3-dioxolane | 90 | P<br>W/W | 28.0 | 2.3<br>0.2 | 5.4<br>0.7 | 14.7<br>6.9<br>0.1 | N.D. | 8.5 |
| 98 | $Co_2(CO)_8$—$Ru_3(CO)_{12}$-3-Pyridyl-5,6-Diphenyl Triazine Disulfonic acid salt | 1,3-dioxolane + 1,3-PDO | 90 | P<br>W/W | 29.0 | 47.4<br>6.9 | 1.5<br>0.2 | 7.0<br>11.7<br>4.8<br>16.5 | N.D. | >20 |

TABLE 17

| EXP. | Catalyst | Solvent | Temp °C. | Time EO Uptake (hr) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 99 | Co—$RuCl_2$ $(C_{10}H_8N_2)_2$—$2H_2O$ | MTBE | 90 | 3 | P<br>W/W | 18.4 | N.D.<br>N.D. | N.D.<br>0.1 | N.D.<br>N.D. | N.D. | <0.1 |
| 100 | Co—$Ru_3(CO)_{12}$-2,2-Bipyridyl | MTBE | 90 | 3¼ | P<br>W/W | 19.9 | 0.4<br>N.D. | 0.2<br>0.8 | <0.1<br>1.2<br>N.D. | N.D. | 1.4 |
| 101 | Co—$Ru_3(CO)_{12}$—$Et_2NCH_2CH_2NEt_2$ | MTBE | 100 | 3 | P<br>W/W | 19.3 | N.D.[a]<br>N.D. | 0.1<br>N.D. | 1.2<br>N.D.<br>N.D. | N.D. | <0.1 |
| 102 | Co—$Ru_3(CO)_{12}$—$Me_2NCH_2CH_2NMe_2$ | MTBE | 100 | 2¾ | P<br>W/W | 19.0 | N.D.<br>N.D. | N.D.<br>N.D. | <0.1<br>N.D.<br>N.D. | N.D. | <0.1 |
| 103 | Co—$Ru_3(CO)_{12}$—$C_{10}H_9N_3$[b] | MTBE | 100 | 3¾ | P<br>W/W | 18.8 | 0.3<br>N.D. | 0.3<br>N.D. | <0.1<br>0.9<br>N.D. | N.D. | 1.0 |
| 104 | Co—1½$Ru_3(CO)_{12}$—1.2$(C_4H_8)NCH_2CH_2N(C_4H_8)$[c] | MTBE | 80 | 3 | P<br>W/W | 19.1 | N.D.<br>N.D. | 0.4<br>N.D. | 0.9<br>N.D.<br>N.D. | N.D. | <0.1 |
| 105 | ½$Co_2(CO)_8$—$Ru_3(CO)_{12}$-½2,2-Bipyridyl[d] | MTBE | >80 | d | P | d | N.D.<br><0.1 | 0.8 | <0.1 | N.D. | <0.1 |

[a]Numerous other product peaks
[b]2,2'Dipyridylamine
[c]1,2-Dipyrrolidinoethane Sample 23768-34
[d]Run in in-situ IR cell, solution spectra recorded

TABLE 18

| EXP. | Catalyst | Solvent | Temp ° C. | Time EO Uptake (hr) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 106 | Co$_2$(CO)$_8$—Ru$_3$(CO)$_{12}$-1.7DIPY | MTBE | 90 | 3¼ | P W/W | 19.9 | 0.4 N.D. | 0.2 0.8 | 1.2 N.D. | N.D. | 1.4 |
| 107 | Co$_2$(CO)$_8$—Ru$_3$(CO)$_{12}$-DIPY | MTBE | 90 | 2¾ | P W/W | 19.1 | 1.1 2.8 | 0.1 0.2 | 1.2 4.4 1.7 | 29 | 7.3 |
| 108 | Co$_2$(CO)$_8$—Ru$_3$(CO)$_{12}$-DIPY | THF | 90$^a$ | 3 | P W/W | 23.5 | 0.8 N.D. | 3.4 N.D. | 6.1 3.6 N.D. | N.D. | 4.2 |
| 109 | Co$_2$(CO)$_8$—Ru$_3$(CO)$_{12}$-DIPY | THF | 100$^{a,b}$ | ¾ | P W/W | 22.2 | N.D. N.D. | 1.5 N.D. | 3.6 N.D. N.D. | N.D. | <0.1 |
| 110 | Co$_2$(CO)$_8$—Ru$_3$(CO)$_{12}$-DIPY | PDO | 90$^a$ | 1 | P W/W | 25.6 | 85.5 19.6 | 0.1 N.D. | N.D. e e | N.D. | e |
| 111 | Co$_2$(CO)$_8$—Ru$_3$(CO)$_{12}$-DIPY | THF$^c$ | 90$^a$ | 1¼ | P W/W | 23.1 | 0.6 N.D. | 4.3 N.D. | e 2.6 N.D. | N.D. | N.D. |
| 112 | Co$_2$(CO)$_8$—[Ru$_3$(CO)$_{10}$(BIPY)]$^d$ | THF$^c$ | 90$^a$ | 3 | P W/W | 24.3 | 0.1 N.D. | 0.7 N.D. | 2.6 0.4 N.D. 0.4 | N.D. | 0.5 |

$^a$Run with ½ (CO/H$_2$) gas
$^b$Half the usual EO charge
$^c$Uninhibited THF solvent
$^d$Product 24090-155
e Run in PDO, No PDO yield calculations

TABLE 19

| EXP. | Catalyst | Solvent | Temp ° C. | Time EO Uptake (hr) | Product Phases | wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 113 | Co$_2$(CO)$_8$—Ru$_3$(CO)$_{12}$-DIPY | 1,3-Dioxolane | 90$^a$ | 2 | P W/W$^b$ | 27.6 | 2.1 N.D. | 3.4 N.D. | 7.9 N.D. | 29 | 9.7 |
| 114 | 2[Co$_2$(CO)$_8$—Ru$_3$(CO)$_{12}$—DIPY | THF | 90$^a$ | 2½ | P W/W | 23.6 | 1.0 N.D. | 2.1 N.D. | 7.9 3.6 N.D. | N.D. | 4.5 |
| 115 | Co$_2$(CO)$_8$-2[Ru$_3$(CO)$_{12}$-DIPY] | 1,3-Dioxolane | 90 | 3 | P W/W | 28.2 | 3.4 N.D. | 6.3 N.D. | 3.6 13.3 N.D. | 22 | 16 |
| 116 | 2[Co$_2$(CO)$_8$-2(Ru$_3$(CO)$_{12}$-DIPY)] | 1,3-Dioxolane | 90 | 2 | P W/W$^b$ | 52.9 | 1.2 N.D. | 4.1 N.D. | 13.3 7.6 N.D. | 16 | 9.3 |
| 117 | Co$_2$(CO)$_8$-2[Ru$_3$(CO)$_{12}$-DIPY]$^c$ | 1,3-Dioxolane | 90$^a$ | 4 | P W/W | 28.0 | 6.3 N.D. | 3.8 N.D. | 7.6 23.7 N.D. | 42 | 31 |
| 118 | Co$_2$(CO)$_8$-2[Ru$_3$(CO)$_{12}$-DIPY]$^c$ | 1,3-Dioxolane | 90$^c$ | 2¾ | P W/W | 28.3 | 6.0 N.D. | 2.7 N.D. | 23.7 25.1 N.D. 25.1 | 43 | 31 |

$^a$Run with ½ (CO/H$_2$) gas
$^b$Small amount of solids in water wash
$^c$No promoter
d Run at 1800 psi with ¼ (CO/H$_2$) Syngas

We claim:

1. A catalyst composition comprising:
   a) A cobalt component comprising one or more non-ligated cobalt carbonyl compounds; and
   b) A ruthenium component comprising a ruthenium carbonyl compound ligated with a N-heterocyclic ligand selected from the group consisting of bidentate and multidentate N-heterocyclic ligands.

2. The composition of claim 1 wherein the N-heterocyclic ligand is a diazine or a benzodiazine.

3. The composition of claim 2 wherein the N-heterocyclic is selected from the group consisting of pyrimidine, pyrazine, pyridazine, quinazoline and quinoxaline.

4. The composition of claim 1 wherein the N-heterocyclic is a bispyridine.

5. The composition of claim 4 wherein the N-heterocyclic is selected from the group consisting of 2,2'-dipyridyl ((DIPY), 2,2'-bipyrimidine (BPYM), 1,10-phenanthroline (PHEN), di-2-pyridyl ketone, 4,4'-dimethyl-2,2'-dipyridyl, 5,6-dimethylphenanthroline, 4,7-dimethylphenanthroline, 2,2'-biquinoline, neocuproine, and 2,2'-dipyridylamine.

6. The composition of claim 1 wherein the N-heterocyclic is a multipyridine.

7. The composition of claim 1 wherein the N-heterocyclic is selected from the group consisting of 2,4,6-tripyridyl-s-triazine (TPTZ), 3,6-di-2-pyridyl-1,2,4,5-tetrazine, 2,2': 6',2"-terpyridine, 2,3-bis(pyridyl)pyrazine, and 3-(2-pyridyl)-5,6-diphenyl-1,2,4-triazine.

8. The composition of claim 1 wherein the N-heterocyclic is a synthesized 2,6-pyridyl-diimine.

9. The composition of claim 8 wherein the synthesized N-heterocyclic is selected from the group consisting of 2,6-bis(N-phenyl, methylimino)pyridine and 2,6-bis[N-(2,6-diisopropylphenyl)methylimino]pyridine.

10. The composition of claim 1 wherein the N-heterocyclic is selected from the group consisting of 2,2'-dipyridyl (DIPY), 2,2'-bipyrimidine (BPYM), and 2,4,6-tripyridyl-s-triazine (TPTZ).

11. The composition of claim 1 wherein the cobalt compound is a cobalt salt that is reduced to the zero valence state by heat treatment in the presence of synthesis gas.

12. The composition of claim 11 wherein the cobalt salt is selected from the group consisting of cobalt carboxylates and cobalt salts of mineral acids, and mixtures thereof.

13. The composition of claim 1 wherein the cobalt compound is a cobalt carbonyl.

14. The composition of claim 13 wherein the cobalt compound is dicobalt octacarbonyl.

15. The composition of claim 1 wherein the ruthenium compound is selected from the group consisting of triruthenium dodecacarbonyl, ruthenium(IV) oxide, ruthenium dicarbonyl acetate polymer, ruthenium(III) chloride, and ruthenium-on-carbon.

16. The composition of claim 15 wherein the ruthenium compound is triruthenium dodecacarbonyl.

17. The composition of claim 1 wherein the ratio of ligand to ruthenium atom is from 2:1 to 1:2.

18. The composition of claim 17 wherein the ratio of ligand to ruthenium atom is about 1:1.

19. The composition of claim 1 further comprising the molar ratio of ruthenium to cobalt is from 4:1 to 1:4.

20. The composition of claim 19 wherein the molar ratio of ruthenium to cobalt is from 2:1 to 1:3.

21. The composition of claim 20 wherein the molar ratio of ruthenium to cobalt is from 1:1 to 1:2.

22. The composition of claim 1 wherein the molar stoichiometry of cobalt: ruthenium: N-ligand is 0.5 to 4 moles: 0.3 to 2 moles: 0.1 to 2 moles.

23. The composition of claim 22 wherein the molar stoichiometry is 1 to 3 moles: 0.5 to 1.5 moles: 0.5 to 1 moles.

24. The composition of claim 1 wherein the cobalt compound is dicobalt octacarbonyl, the ruthenium compound is triruthenium dodecacarbonyl, and the N-heterocyclic ligand is 2,2'-bipyrimidine or 2,2'-dipyridyl.

25. The composition of claim 24 wherein the composition has a molar stoichiometry of Co—Ru-ligand of 2:1:1 to 1:1:1.

26. The composition of claim 1 wherein the cobalt compound is dicobalt octacarbonyl, the ruthenium compound is triruthenium dodecacarbonyl, and the N-ligand is 2,4,6-tripyridyl-s-triazine.

27. The composition of claim 26 further comprising the ratio of Co:Ru:ligand is about 2:1:0.7.

28. The composition of claim 27 further comprising being characterized by a cobalt carbonyl anion IR band in the range 1875 to 1900 cm$^{-1}$.

29. A catalyst composition comprising:
   a) A cobalt component comprising one or more non-ligated cobalt carbonyl compounds; and
   b) A ruthenium component comprising a ruthenium carbonyl compound ligated with a N-heterocyclic ligand.

30. The composition of claim 1 wherein the N-heterocyclic is a pyridine.

31. The composition of claim 30 wherein the N-heterocyclic is selected from the group consisting of pyridine, 3-hydroxypyridine, and quinoline.

32. The composition of claim 31 wherein the N-heterocyclic is selected from the group consisting of lower cost homologues of 3-hydroxypyridine and quinoline derived from coal-tar extracts.

* * * * *